United States Patent [19]

Rebafka et al.

[11] Patent Number: 4,521,602
[45] Date of Patent: Jun. 4, 1985

[54] PREPARATION OF PYRIDINES OR PYRROLES FROM $\alpha,\omega$-DINITRILES

[75] Inventors: Walter Rebafka, Eppelheim; Gerd Heilen, Speyer; Klaus Halbritter, Mannheim; Wolfgang Franzischka, Ludwigshafen, all of Fed. Rep. of Germany

[73] Assignee: BASF Aktiengesellschaft, Fed. Rep. of Germany

[21] Appl. No.: 502,522

[22] Filed: Jun. 9, 1983

Related U.S. Application Data

[63] Continuation of Ser. No. 347,162, Feb. 9, 1982, abandoned.

[30] Foreign Application Priority Data

Feb. 11, 1981 [DE] Fed. Rep. of Germany ....... 3104765

[51] Int. Cl.³ .................. C07D 211/10; C07D 213/08; C07D 207/32
[52] U.S. Cl. ................. 546/184; 546/250; 546/251; 548/564
[58] Field of Search ....... 546/184, 250, 251; 548/564

[56] References Cited

U.S. PATENT DOCUMENTS

| | | | |
|---|---|---|---|
| 4,276,419 | 6/1981 | Verheijen et al. | 546/164 |
| 4,294,968 | 10/1981 | Stone et al. | 546/251 |
| 4,386,207 | 5/1983 | de Graaf et al. | 546/184 |

*Primary Examiner*—Alan L. Rotman
*Attorney, Agent, or Firm*—Keil & Weinkauf

[57] ABSTRACT

A pyridine or a pyrrole is obtained in a one-stage process directly from an $\alpha,\omega$-dinitrile of appropriate carbon skeleton when the dinitrile is reacted in the gas phase with hydrogen, over a hydrogenation catalyst.

5 Claims, No Drawings

PREPARATION OF PYRIDINES OR PYRROLES FROM α,ω-DINITRILES

This is a continuation of application Ser. No. 347,162 filed Feb. 9, 1982, now abandoned.

It has been disclosed that pyridine can be prepared from glutarodinitrile in two steps by initially preparing the corresponding diamine in a pressure reaction in the liquid phase, over a nickel or cobalt catalyst; varying amounts of piperidine are formed as by-product, and its formation can also be promoted by certain measures (Freidlin et al., Dokl.Akad. Nauk. USSR (1962), 625 et seq., and German Published Application DAS No. 2,514,004). Pentamethylenediamine as well as piperidine can be dehydrogenated in the gas phase to give pyridine.

The conversion of an α, ω-dinitrile in the liquid or gas phase to give a diamine or aminonitrile has also been disclosed; Belgian Patent No. 751,254 describes the use of iron (oxide) as a catalyst, while South African Patent Application No. 39,237/67 recommends the use of nickel.

The particular problem of the one-stage conversion of a dinitrile to an aromatic or pseudoaromatic heterocyclic ring system arises from the fact that the dinitrile is thermally relatively unstable, whereas the dehydrogenation of the diamine formed as an intermediate (and stable per se) requires relatively severe conditions.

It is an object of the present invention to find a solution to the above problem.

We have found that this object is achieved and that dinitriles of appropriate carbon skeleton can be directly converted into pyridine or pyrrole or their substitution products when they are reacted in the gas phase with hydrogen, in the presence of a hydrogenation catalyst which preferably contains a platinum metal.

Hydrogenation catalysts containing palladium or platinum as the active constituent are preferably used; catalysts containing metals, which are active in hydrogenation, of group 1b of the periodic table, ie. copper, and of group 2b, in particular zinc or zinc oxide, are also suitable. Experience has shown cobalt to be less suitable.

In some cases it has proved useful to employ additional metals, and vanadium and/or copper are thus added to palladium, for example as recommended in German Laid-Open Application DOS No. 2,839,135.

It is advantageous to use a catalyst which contains a conventional carrier for the particular active metal. Particularly frequently recommended carriers are aluminum oxide of various structures, spinels, silicates, silica, other thermally stable oxides, eg. those of titanium, zirconium and magnesium, and, for example, carbonates of alkaline earth metals, as well as carbides, and carbon and naturally occurring carriers, eg. pumice or kieselguhr.

Experience has shown that a special choice of carrier is not necessary, but aluminum oxides and synthetic spinels have proved useful.

The active metals, when noble metals, are used in conventional small amounts, for example less than a few percent, and when copper or zinc, in general in an amount of 10 or 20 percent or more, or the carrier is even dispensed with if not required for mechanical reasons.

The conventional technology for a gas phase reaction can be used, and examples of suitable reactors are tubular reactors, fluidized beds or shaft reactors, which also determine the external form of the catalyst.

The reaction temperature should be as low as possible, but in general 150° C. or higher. It must be noted that the jacket temperature of the reaction space often does not correspond to the actual temperature at the catalyst surface, and the temperature should therefore be measured, as far as possible, within the gas space.

The reaction is conventionally carried out under atmospheric pressure or in a range close to this; if the particular boiling point of the starting material is nevertheless reached, the reaction space can be better utilized by slightly increasing the pressure.

Hydrogen is preferably used in an excess, which can be, for example, from 2 to 100 times the theoretically required amount. In general a 10-fold excess is sufficient.

Dinitriles required for the preparation of pyridines are glutarodinitrile and its substitution products. They can be monosubstituted at any $CH_2$ group; of commercial significance is substitution by a short alkyl group in the 2-position or 3-position, which leads to β-or γ-picoline and its 3- or 4-alkyl homologs, and thus simplifies the route to nicotinic acid or isonicotinic acid and derivatives thereof.

Correspondingly, succinonitriles give pyrrole and its products substituted in the 3-position and/or 4-position, in particular the alkyl derivatives.

The products obtainable by condensation after passing through the reaction zone can contain, in addition to the particular desired product, also products of partial conversion, ie. the corresponding diamine and the saturated cyclic amine. Clearly, these compounds, which are usually easy to isolate, can be recycled, and their formation thus implies no reduction in the yield or selectivity of the reaction.

The practicability of the invention was investigated, inter alia, by the following experiments:

EXAMPLE 1

A tube made of V2A stainless steel, having a diameter of 10 mm and a length of 250 mm, and containing 200 ml of a catalyst which consists of 0.7% of Pd on $Al_2O_3$ is charged, per hour, with 23 l of hydrogen containing 23 g of vaporized 2-methylglutarodinitrile. The external temperature of the tube is 280° C.

The reaction products are condensed and collected. After 10 hours, 189 g of condensate have separated out and are distilled and investigated by gas chromatography. 184 g of β-picoline and 13 g of 3-methylpiperidine are found, corresponding to a total yield of 83%.

EXAMPLE 2

A tube made of V2A stainless steel, having a diameter of 10 mm and a length of 500 mm, and containing 26 g of a catalyst (0.35% of Pt/$Al_2O_3$) is heated to 250° C., and is then charged in the course of 10 hours with 85 g of 2-methylglutarodinitrile vaporized in 180 l of hydrogen. 76 g of a mixture consisting of 13% of 3-methylpiperidine, 50% of β-picoline, 0.2% of 2-methylglutarodinitrile and residual unidentified products are obtained.

The yield is 70%, based on the dinitrile employed, and taking the piperidine into account.

EXAMPLE 3

A quartz tube, having a diameter of 30 mm and a length of 500 mm, and containing 220 ml of a catalyst which consists of 1% of palladium on a lithium aluminum spinel is fed, per hour, with 20 ml of a mixture containing 89% of 2-methylglutarodinitrile and 10% of 2-ethylsuccinodinitrile, vaporized in 200 l of hydrogen. The external temperature of the quartz tube is 250° C. The reaction products are condensed and collected until 2,023 g of the dinitrile mixture have been consumed. 1,687 g of a condensate containing 40% by weight of β-picoline and 37% by weight of methylpiperidine are obtained. This corresponds to a yield of 81%, based on the 2-methylglutarodinitrile employed.

EXAMPLE 4

2.5 g of glutarodinitrile and 10 l of hydrogen, per hour, are reacted as described in Example 2, at a jacket temperature of 250° C., over 20 g of a catalyst (0.5% of Pd on $Al_2O_3$).

After 20 hours, the resulting condensate is investigated. 20 g of pyridine and 12 g of piperidine are found. Yield: 75%

EXAMPLE 5

100 ml per hour of 2-methylglutarodinitrile (90% strength) and 350 l per hour of hydrogen are fed to a fluidized bed which contains 1 l of catalyst (5% of palladium and 0.25% of selenium on active charcoal) and is maintained at 310° C.

3.7% of 3-methylpiperidine, 66% of β-picoline and 11% of 2-methylglutarodinitrile, as well as unidentified compounds, are found.

The selectivity is 75%, based on 2-methylglutarodinitrile converted.

We claim:

1. A process for the preparation of pyridine or pyrrole or their lower alkyl-substituted products which comprises: reacting unsubstituted glutarodinitrile, lower alkyl-substituted glutarodinitrile, unsubstituted succinodinitrile or lower alkyl-substituted succinodinitrile or mixtures thereof with a 2- to 100-fold excess of gaseous hydrogen, said reaction being conducted in the gas phase, at essentially atmospheric pressure, in the presence of a conventionally supported or unsupported platinum-metal hydrogenation catalyst, and at a temperature above 150° C. but below the decomposition temperatures of the dinitrile reactant and the resulting reaction product.

2. The process of claim 1 wherein 2-methyl glutarodinitrile is reacted with hydrogen to form β-picoline.

3. The process of claim 1 wherein 2-ethyl succinodinitrile is reacted with hydrogen to form 2-methylpiperidine.

4. The process of claim 1 wherein glutarodinitrile is reacted with hydrogen to form pyridine.

5. The process of claim 1 wherein the active catalyst component is platinum and/or palladium.

* * * * *